United States Patent [19]
Kim et al.

[11] Patent Number: 5,866,428
[45] Date of Patent: Feb. 2, 1999

[54] CYANIDE-FREE REAGENT AND METHOD FOR THE DETERMINATION OF HEMOGLOBIN

[75] Inventors: Young Ran Kim, Sunnyvale, Calif.; Stephen D. Stroupe, Libertyville, Ill.

[73] Assignee: Abbott Laboratories, Abbott Park, Ill.

[21] Appl. No.: 730,193

[22] Filed: Oct. 15, 1996

Related U.S. Application Data

[62] Division of Ser. No. 524,128, Aug. 31, 1995, Pat. No. 5,612,223, which is a continuation of Ser. No. 212,626, Mar. 11, 1994, abandoned.

[51] Int. Cl.⁶ .................................................. G01N 33/72
[52] U.S. Cl. ................................ 436/66; 436/8; 436/17; 436/63; 436/166; 436/177; 424/93.73
[58] Field of Search .................................. 436/8, 17, 18, 436/63, 66, 166, 177; 424/93.73

[56] References Cited

U.S. PATENT DOCUMENTS

| | | | |
|---|---|---|---|
| 4,200,435 | 4/1980 | Stroupe et al. | 436/67 |
| 4,255,385 | 3/1981 | Stroupe et al. | 422/61 |
| 4,274,978 | 6/1981 | Moore | 436/15 |
| 4,853,338 | 8/1989 | Benezra et al. | 436/66 |
| 5,242,832 | 9/1993 | Sakata | 436/17 |
| 5,506,144 | 4/1996 | Sundrehagen | 436/66 |

OTHER PUBLICATIONS

R. Zander, et al., "Alkaline haematin D–575, a new tool for the determination of haemoglobin as an alternative to the cyanhaemiglobin method. I. Description of the method", *Elsevier Science Publishers*, 83–93 (1984).

M.J. Malin, et al, "Mechanism of automated alkaline methods for the determination of hemoglobin in whole blood based on the micellization of ligated heme in the presence and absence of cyanide", *Analytica Chemica Acta*, 262 (1992) 67–77.

*Primary Examiner*—Maureen M. Wallenhorst
*Attorney, Agent, or Firm*—David L. Weinstein

[57] ABSTRACT

A cyanide-free method and reagent for determining the concentration of total hemoglobin in a whole blood sample accurately in less than 10 seconds including a ligand selected from the group consisting of imidiazole, imidazole derivatives, N-hydroxyacetamide, N-hydroxyl amine, pyridine, oxazole, thiazole, pyrazole, pyrimidine, purine, quinoline, and isoquinoline, and a surfactant with strong erythrolytic capability selected from the group consisting of lauryl dimethylamine oxide and octylphenoxy polyethoxyethanol. The reagent pH is adjusted to about 11 to about 14. Rapid mixing of the reagent with a blood sample leads to the formation of a stable chromogen whose absorbance can be measured between 540 and 550 nm. The cyanide-free reagent is ideal for use on an automated high through-put clinical hematology analyzer.

7 Claims, 4 Drawing Sheets

FIG. 5(A) CONTROL REAGENT

FIG. 5(B) STORED AT 45°C FOR 3 MONTHS 5,866,428

CYANIDE-FREE REAGENT AND METHOD FOR THE DETERMINATION OF HEMOGLOBIN

This is a divisional of U.S. patent application Ser. No. 08/524,128, filed Aug. 31, 1995 and now U.S. Pat. No. 5,612,223, issued on Mar. 18, 1997, which is a continuation of U.S. patent application Ser. No. 08/212,626, filed on Mar. 11, 1994 and now abandoned.

TECHNICAL FIELD

The present invention relates generally to reagents and methods for use in determining the concentration of hemoglobin present in a whole blood sample, either in manual methods or automated methods. The specific reagent rapidly converts all of the hemoglobin in the sample into a well defined chromogen for detection and measurement, without the use of cyanide.

BACKGROUND OF THE INVENTION

The science of hematology has long recognized the importance of measuring the amount of hemoglobin in a blood sample since it is the hemoglobin molecule which transports oxygen from the lungs to the various tissues and organs of the body. The accurate measurement of hemoglobin concentration in a patient's blood is arguably the most important parameter determined in a hematology analysis. The hemoglobin concentration is used to screen for anemia which in turn is a sign of underlying disease.

In countries with a "Western Diet", a hemoglobin concentration below 14 grams per deciliter (g/dL) in men and 12 g/dL in women is indicative of anemia. The causes of anemia are many and a low hemoglobin concentration is a strong signal for a thorough workup by the patient's physician. Therefore an accurate and reliable method for measuring hemoglobin concentration is a vital part of any hematology system. The two most common reasons for a patient to be anemic are blood loss and dietary deficiencies in iron, vitamin B12, or Folic Acid. In the former case it is mandatory for the physician to determine the cause of the blood loss and treat it. And again in the latter case, a proper diagnosis is needed to define the appropriate nutritional supplemental treatment.

In addition to its importance as the primary indicator of anemia, the hemoglobin concentration is used in combination with other blood cell parameters to calculate several indices. The Mean Corpuscular Hemoglobin (MCH) is the mass of hemoglobin per red cell and is calculated by dividing the hemoglobin concentration by the number of Red Blood Cells in the comparable volume. The Mean Corpuscular Hemoglobin Concentration (MCHC) is the weight percent of hemoglobin in a Red Blood Cell and is calculated by dividing the hemoglobin concentration by the hematocrit and converting to percent. Both MCH and MCHC are useful parameters in the diagnosis of an anemia. Their importance further emphasizes the necessity of making an accurate and reliable measurement of the hemoglobin concentration in a blood sample.

Modern methods of measuring the hemoglobin content utilize spectrophotometry to quantitate the amount of the oxygen-carrying protein in the sample. The requirements of any spectrophotometric method to measure hemoglobin in a blood sample are two-fold:

1. The method must release all the hemoglobin from the red blood cell in which it is sequestered; and 2. The method must convert all the hemoglobin in the sample into a single chromogenic species, regardless of what form the hemoglobin is in when the reaction is begun.

The first requirement can be achieved by many means; the simplest being to dilute the blood sample in distilled water to effect a hypotonic lysis. However, modern automated hematology instruments require a more rapid lysis than can be achieved with hypotonic lysis. Frequently, surfactants are added to the lysing reagent to hasten the release of hemoglobin and to clear any turbidity which may be in the sample due to elevated lipid content. Various kinds of surfactants are suitable for this task, including anionic, non-ionic, zwitterionic, and cationic. The amount of surfactant required can range from about 100 mg/L to about 50 g/L, depending on the "potency" of the surfactant and the ionic strength of the reagent.

The second requirement necessitates an understanding of the chemistry of the heme iron which carries oxygen when complexed in a globin protein molecule. The heme iron is maintained in the +2 ($Fe^{II}$) oxidation state in a normal blood sample. Since the blood sample is usually taken from a vein, the hemoglobin is mostly in the de-oxy state; that is, no oxygen is bound to the heme iron. However, as soon as the sample comes into contact with the atmosphere or is diluted into an oxygen containing buffer or lysing reagent, it is rapidly converted into oxy-hemoglobin; the heme iron binds oxygen but stays in the $Fe^{II}$ (reduced) state. In many cases, the amount of hemoglobin in the sample could be determined from the oxy-hemoglobin chromogen which is formed naturally upon exposure to air. However, there are some conditions which make this simple solution unacceptable. In some diseases, genetic conditions, or poisonings, a patient may have a significant amount of met hemoglobin in circulation. In met hemoglobin, the heme iron is in the +3, ($Fe^{III}$) oxidized state. It cannot bind oxygen, nor can it readily be reduced to $Fe^{II}$ so that it can bind oxygen to be measured as oxy hemoglobin. Also, heavy cigarette smokers and workers exposed to high concentrations of automobile exhaust frequently accumulate a high concentration of carbon monoxide bound to their heme iron. Carbon monoxide is tightly bound and blocks the binding of oxygen, thereby causing an error in the concentration of hemoglobin if determined by the oxy hemoglobin method. The most commonly used approach to the measurement of hemoglobin is to oxidize all the heme iron to the +3 state and to introduce a ligand which will quantitatively bind to all the heme iron to produce a single chromogenic species for quantitation by spectrophotometry.

The classical method is that of Drabkin. Briefly, the hemoglobin is released by hypotonic lysis (modern adaptations have added surfactants to speed the lysis), the heme iron is oxidized to $Fe^{III}$ by means of potassium ferricyanide, and the iron reacted with the cyanide anion of potassium cyanide. Cyanide binds very tightly to $Fe^{III}$ and gives a distinctive chromogen with a peak at about 540 nm. Recent adaptations have involved the deletion of the ferricyanide oxidizing agent and have depended on the oxidation of the heme iron by atmospheric oxygen (or oxygen equilibrated reagents) at elevated pH in the presence of surfactants; cyanide is still used as the heme iron ligand in most procedures in spite of its well-known toxicity.

Many automated hematology analyzers utilize a modification of Drabkin's method. In these methods, red cells are lysed by a cationic surfactant at pH above 10 in the presence of cyanide. Under these conditions, white cell nuclei remain intact and can be counted by common impedance methods. Hemoglobin is measured by taking the optical density of the same solution at 540 nm, as is customarily done with Drabkin's method. The method can yield erroneous measurements in samples which have a high white cell count because of turbidity due to scattering of light by the nuclei. Lipemic and icteric samples also can interfere due to turbidity or increased absorbance of the sample. The present invention avoids these problems by providing a reagent which measures hemoglobin free from interference due to other blood components.

Stroupe, et al. (U.S. Pat. No. 4,200,435) disclose the use of imidazole as a ligand for the determination of glycosylated hemoglobin in the presence of an allosteric effector. They also disclose the use of a surfactant lysing agent, an oxidizing agent, and a heme-binding ligand to determine the amount of hemoglobin in a sample. Stroupe, et at. (U.S. Pat. No. 4,255,385) also disclose reagent kits containing the above reagents. The present invention differs from that disclosed by the Stroupe, et al. patents in that it requires no added oxidizing agent and in that the reaction is completed within 10 seconds as opposed to approximately 10 minutes in the prior art invention.

Benezra, et al. (U.S. Pat. No. 4,853,338) disclose a cyanide-free hemoglobin reagent which comprises a very high surfactant concentration (20 to 50 g/L) and a pH between 11.3 and 13.7. From the elevated pH, and the large amount of $N_aOH$ required to achieve the desired pH, it can be inferred that the heme-binding ligand of this invention is the hydroxide anion. If the hydroxide ion content of the reagent is not high enough, the heme will not be converted stoichiometrically to a single chromogen since water which is present at high (55M) concentration will compete for iron binding sites and may give an erroneous result. The present invention avoids this problem.

It is an object of the present invention to provide a cyanide-free method and reagent for the determination of total hemoglobin present in a whole blood sample. It is a further object of this invention to provide a rapid method for total hemoglobin determination which can be used on automated instruments. It is another object of this invention to provide a cost effective reagent. It is another object of this invention to provide a method for total hemoglobin determination in whole blood without the interference of other blood components.

These and further objects of the invention will become apparent to those of ordinary skill in the art from the following description and figures.

SUMMARY OF THE INVENTION

A cyanide-free reagent for use in a hemoglobin determination method comprises an aqueous solution of (i) a cyanide-free ligand selected from the group consisting of imidazole, imidazole derivatives, N-hydroxyacetamide, N-hydroxyl amine, pyridine, oxazole, thiazole, pyrazole, pyrimidine, purine, quinoline, and isoquinoline, and present at a concentration of 0.1 to 2.0 Molar and (ii) a strong erythrolytic surfactant selected from the group consisting of lauryl dimethylamine oxide and octylphenoxy ethanol, and present in an amount from about 0.1% to about 1.0 % (w/v), the pH of the reagent being adjusted to 11–14, preferably with a monovalent base. According to the method of the invention, the cyanide-free reagent is rapidly mixed with the blood sample to form a chromogen. The absorbance, or optical density, of the resulting chromogen is then measured as an indication of the concentration of hemoglobin. The chromogen formed in this method can be obtained in approximately ten (10) seconds, making it especially well suited for use in automated instruments.

DETAILED DESCRIPTION OF THE INVENTION

The reagent of the present invention was developed for the total hemoglobin analysis when used on a high throughput automated hematology instrument.

A reagent useful for hemoglobin determination must be able to quickly lyse the erythrocytes and rapidly complex with the hemoglobin so that a detectable chromogenic structure is formed for detection and measurement. The present invention is particularly advantageous because the complex is formed rapidly and remains stable for a period of time compatible with automated instruments. The reactant is stable for many weeks. The present invention is also particularly advantageous because the resulting chromogen appears to be free of interference from other blood components and can be measured at wavelengths in the spectral range of automated hematology instruments already in the field. For comparison purposes, the cyan met hemoglobin method typically measures absorbance at 540 nm. A reddish brown chromogen can be formed according to the present invention which has an absorption maximum at about 544 nm.

The reagent of the present invention is an aqueous solution of a ligand-forming compound such as imidazole and imidazole derivatives. The ligand-forming compound is present at concentrations of 0.1M to 2.0M. Inidazole, from the present reagent, ligates with the hemoglobin which is released from the erythrocytes in the sample. Other ligand-forming compounds useful in the present invention include N-hydroxyacetamide, N-hydroxyl amine, pyridine, oxazole, thiazole, pyrazole, pyrimidine, purine, quinoline, and isoquinoline. Anions which can bind the oxidized iron heme include cyanate, fluoride, azide, nitrite, hydroxide, acetate, and formate; acceptable salts of these anions include sodium, potassium, ammonium, and the like.

The reagent further contains a surfactant with a strong erythrolytic capability. Lauryl dimethylamine oxide (Ammonix L.O.) [Stepan Chemical Company, Northfield, Ill.], and octylphenoxy polyethoxyethanol (Triton X 100) or other strong detergents may be used as the surfactant component of the lysing reagent. The surfactant should be present at concentrations from about 0.1% to about 1.0% (w/v). The pH of the reagent should be adjusted to between 11 and 14, preferably 12.5. Monovalent bases such as sodium hydroxide and potassium hydroxide may be utilized for pH adjustment.

According to the method of the present invention, the lysing reagent is mixed with a whole blood sample in the ratio of approximately 50 –1000:1 reagent to blood. The sample and reagent can be rapidly mixed to achieve erythrolysis and conversion of hemoglobin to the chromogen. The sample and reagent mixture may then be presented to an absorbance spectrophotometer where the optical density of the chromogen formed is measured. When the ligand is imidazole the measurement can be made between 540 nm and 550 nm. The total hemoglobin concentration in the sample is related to the optical density of the converted chromogen.

The invention will now be described with reference to examples which are intended to illustrate and not limit the scope of the claimed invention.

EXAMPLE 1

0.4 Moles of imidazole (27.2 g) (Sigma Chemical Company) and 0.1 mole of sodium hydroxide (4.0 g) (Fisher Chemical Company) were added to approximately 900 ml of distilled water in a graduated cylinder. The reagents were dissolved using a magnetic stirrer. 3.3 mL of lauryl dimethylamine oxide (nonionic surfactant, 30% solution, Stepan Chemical Company, Northfield, Ill.) was added with stirring and the volume adjusted to 1000 ml by addition of distilled water. The solution was filtered through a 0.2 micron Nalgene filter and stored at room temperature until used. This formulation is subsequently referred to as Imidazole 0.4.

Other reagents were prepared in the same manner except that the amount of imidazole was varied between 0.1 mole (6.8 g) and 1.0 mole (68.1 g). These formulations are subsequently referred to as Imidazole "X" where X refers to the molar concentration.

EXAMPLE 2

Figure 1:
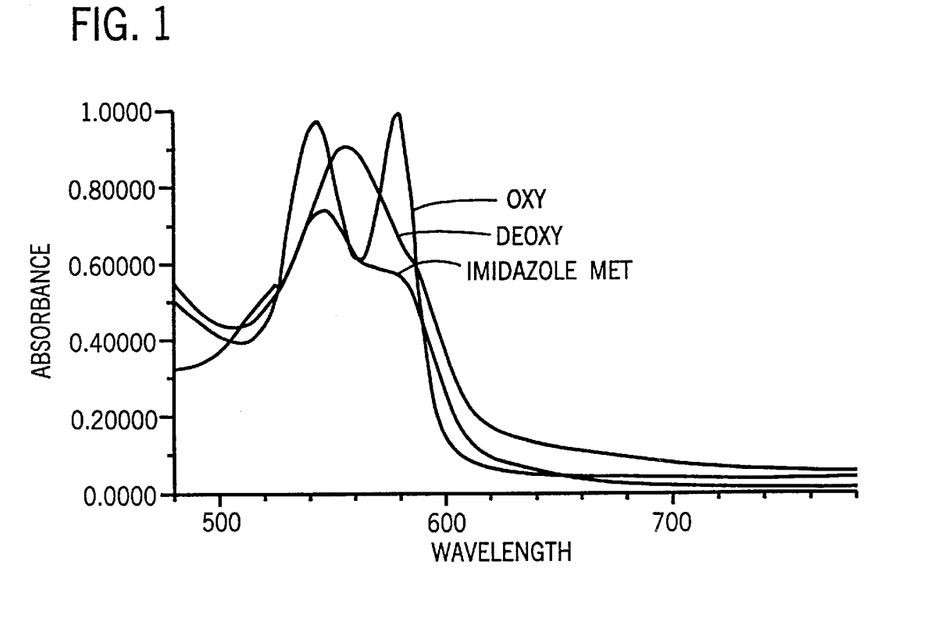
FIG. 1 is a spectrum of a sample prepared using the method and reagent of the present invention.

Twelve (12) microliters of whole blood was mixed with 3.0 mL of Imidazole 0.4. The absorption spectrum was recorded from 780 nm to 480 nm with a Hewlett Packard 8452A Diode Array Spectrophotometer ("HP"). FIG. 1 shows a peak at 544 nm with a shoulder around 580 nm. For comparison, the spectra of oxy and de-oxy hemoglobin at the same concentration are included.

EXAMPLE 3

Whole blood (12) microliters was rapidly mixed with 3.0 ml of Imidazole reagents ranging from 0.1 to 1.0M. The absorbance was monitored at 544 nm for 60 seconds. The change in absorbance between 10 seconds post mix and 60 seconds post mix was measures and tabulated as "drift."

| Imidazole Conc. | Drift (mA) |
|---|---|
| 0.1 | −80 |
| 0.25 | −10 |
| 0.4 | 0 |
| 0.66 | 0 |
| 1.0 | 0 |

EXAMPLE 4

A series of formulations with varying NaOH, surfactant and imidazole concentrations were made and tested for completeness of lysis and stability of signal. Twelve (12) microliters of whole blood were mixed with reagent. Absorbance at 700 nm was observed for completeness of lysis and at 544 nm for completeness of the conversion to chromogen. Completeness of lysis is indicated by a "+"; presence of drift is indicated by a "+"; "++" indicates pronounced drift.

Although it is desirable to have the reaction complete, that is complete lysis and lack of drift, within a short period of time, it is possible to use a drifting signal if the timing of reagent addition and absorbance measurement is controlled.

| NaOH (M) | Ammonix LO (%) | Imidazole | Lysis | Drift |
|---|---|---|---|---|
| 0.01 | 0.01 | 0.1 | + | + |
| 0.01 | 0.01 | 1.0 | − | ++ |
| 0.01 | 0.1 | 0.1 | + | + |
| 0.01 | 0.1 | 1.0 | + | − |
| 0.1 | 0.01 | 0.1 | + | + |
| 0.1 | 0.1 | 1.0 | + | − |
| 0.1 | 0.01 | 0.1 | + | + |
| 0.1 | 0.1 | 1.0 | + | − |

EXAMPLE 5

For this and Examples 6 and 7, Imidazole 0.4 was used exclusively. Manipulated blood samples were prepared to give a range of hematocrit values. The samples were prepared by centrifuging an EDTA anticoagulated blood sample at 500 g for 10 minutes. The plasma was added to a normal blood sample to prepare a reduced hematocrit sample. The buffy coat was reserved to give an elevated white blood cell count sample with a normal hematocrit. The sedimented red blood cells were analyzed as an elevated hematocrit sample. Hematocrits and white blood cell counts were determined on a Baker 4000 analyzer. The absorbance of the sample diluted 1 to 1:251 with Imidazole 0.4 was read at 540 nm on a Hewlett-Packard 8452A Diode Array Spectrophotometer. The results are shown below.

| Sample | Hematocrit | WBC Count | Absorbance (mA) |
|---|---|---|---|
| Low | 10.6 | 0.7 | 105.6 |
| High WBC | 45.9 | 19.1 | 421.0 |
| Normal | 42.0 | 7.3 | 397.5 |
| High | 74.1 | 8.0 | 722.5 |

EXAMPLE 6

A kit for the determination of hemoglobin by the method of Drabkin was used to compare the performance of the Imidazole 0.4 reagent with an established reference method. The kit, Catalog No. 525-A, was obtained from Sigma Diagnostics, P. O. Box 14508, St. Louis, Mo., 63178, and was reconstituted and used according to the instructions.

A normal sample of whole blood was manipulated to give hemoglobin concentrations from zero to approximately 20 g/dL. Samples were analyzed by the Drabkin's method and using Imidazole 0.4. The Drabkin's sample was reacted at a 1 to 251 ratio and the Imidazole 0.4 at a ratio of 1 to 101. All reaction mixtures were read at 540 nm in a Hewlett Packard Diode Array Spectrophotometer. Although the Irnidazole 0.4 reaction is complete within 10 seconds, the reaction mixtures were allowed to incubate for approximately 30 minutes before reading for convenience.

| Sample | Hb by Drabkin's | Imidazole A540 (mA) |
|---|---|---|
| 1 | 0 | 0.6 |
| 2 | 2.8 | 204.4 |
| 3 | 7.1 | 511.5 |
| 4 | 9.9 | 735.4 |

-continued

| Sample | Hb by Drabkin's | Imidazole A540 (mA) |
|---|---|---|
| 5 | 13.9 | 983.7 |
| 6 | 15.2 | 1148.6 |
| 7 | 15.9 | 1182.0 |
| 8 | 17.2 | 1242.1 |
| 9 | 17.6 | 1348.8 |
| 10 | 19.8 | 1435.3 |
| 11 | 19.9 | 1545.0 |

The correlation coefficient of the Imidazole 0.4 reagent with the Drabkin's reagent is r=+0.9976, the Slope is 75.2 mA/g/dL, and the intercept is −12.0 mA. The excellent linear correlation of the A540 given by the Imidazole 0.4 reagent with the standard Drabkin's reagent demonstrates the equivalence of results by the two methods and allows the use of the non-poisonous formulation of the current invention instead of the cyanide containing standard method.

EXAMPLE 7

The Imidazole 0.4 reagent was compared to a commercially available, semi-automated hematology analyzer, the Coulter JT, using Lysis S III (which contains potassium cyanide) and Isoton III reagents, [all from Coulter Diagnostics, Hialeah, Fla.] A series of manipulated whole blood samples were prepared as above with hemoglobin concentrations ranging from 0 to about 25 g/dL. The samples were analyzed on the Coulter JT analyzer as described in the instrument's manual. The Imidazole 0.4 reagent was reacted with samples at a ratio of 1 to 126 by dispensing 40 microliters blood sample using a positive displacement pipette (Absoluter Pipettor, Tri-Continent Scientific Company, Grass Valley, Calif.) into a tube and adding 5.0 ml of the Imidazole 0.4 reagent with an Eppendorf Repipettor (Brinkman Instruments, Inc., Westbury, N.Y.) The absorbance at 540 nm of the reacted samples was read on a Beckman DU-7 Spectrophotometer (Beckman Instruments, Fullerton, Calif.) equipped with a sipper. Determinations with the Imidazole 0.4 were made in duplicate and the results averaged.

The strong linear correlation (correlation coefficient, r=0.9998; Slope, m=49.94 mA/g/dL, intercept b=4.4 mA) demonstrates that the current invention gives results strictly comparable to the known commercial instrument.

| Sample | Coulter (g/dL) | Imidazole A540 (mA) |
|---|---|---|
| 1 | 0.1 | −0.4 |
| 2 | 5.5 | 283.6 |
| 3 | 8.0 | 406.6 |
| 4 | 10.6 | 535.2 |
| 5 | 12.8 | 645.7 |
| 6 | 14.3 | 732.5 |
| 7 | 18.7 | 935.2 |
| 8 | 19.8 | 983.6 |
| 9 | 20.3 | 1016.2 |
| 10 | 26.0 | 1303.4 |

EXAMPLE 8

Fifty-two clinical samples, whose hemoglobin concentration ranged from 12 g/dL to 17.5 g/dL, were analyzed on a calibrated Cell-Dyn 3500 system, a fully automated hematology analyzer currently sold by Abbott Laboratories, Diagnostics Division, Santa Clara, Calif., and also on a fully automated, experimental hematology analyzer under development along with the current invention (However, any automated hematology analyzer could easily be adapted to accept the reagent and method of this invention.). The Cell-Dyn 3500 hemoglobin reagent contains potassium cyanide and the reactant of blood hemoglobin is cyanmethemoglobin. The whole blood dilution factor for hemoglobin measurement is 1:301 and the detection wavelength of the reactant is 540 nm. The experimental hemoglobin reagent contains 0.4 moles of imidazole, 0.1 mole of sodium hydroxide, and 0.1% (w/v) lauryl dimethylamine oxide in deionized water. The pH of the reagent was 13.0 without adjustment. The whole blood dilution factor for the CD 3500 hemoglobin measurement in the system is 1:125 and the reaction time is 10 seconds. The detection wavelength of the converted chromogen is 540 nm. The hemoglobin results of the experimental analyzer were then compared to that of the Cell-Dyn 3500 by linear regression analysis.

Figure 2:
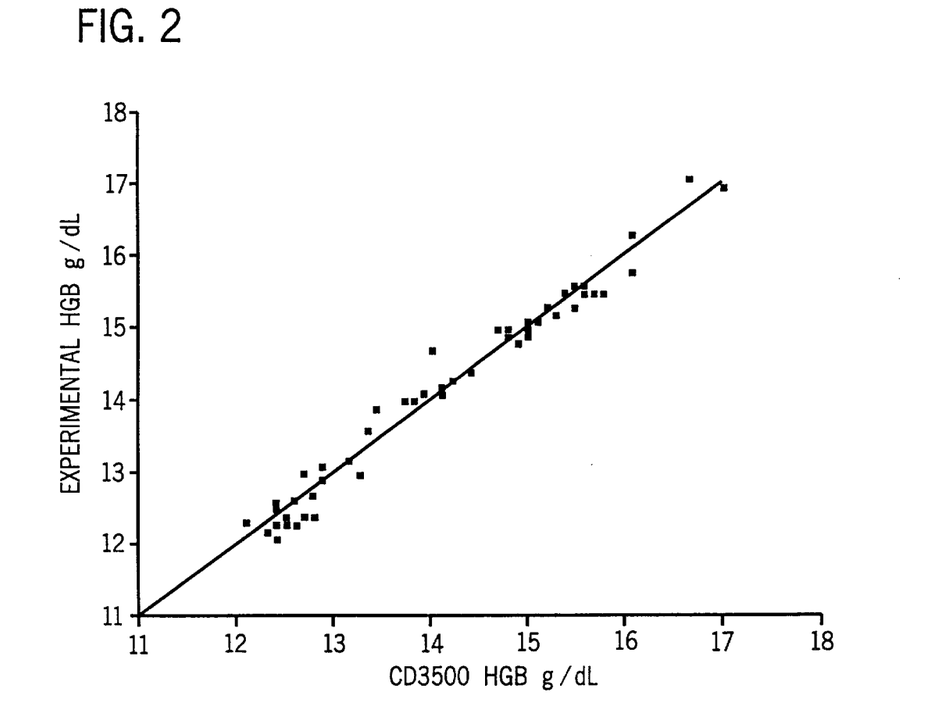
FIG. 2 is a correlation plot of hemoglobin data obtained using a cyanide-containing hemoglobin method performed on a Cell-Dyn analyzer vs. the cyanide-free hemoglobin method of this invention which was performed on an experimental, automated hematology analyzer.

As can be seen in the regression statistics in FIG. 2, the performance of the two methods is essentially equivalent. Correlation coefficient=0.99; Slope=0.97; and Y-Intercept=0.34.

The strong linear correlation demonstrates that the current invention gives results strictly comparable to the known commercial instrument.

EXAMPLE 9

Figure 3:
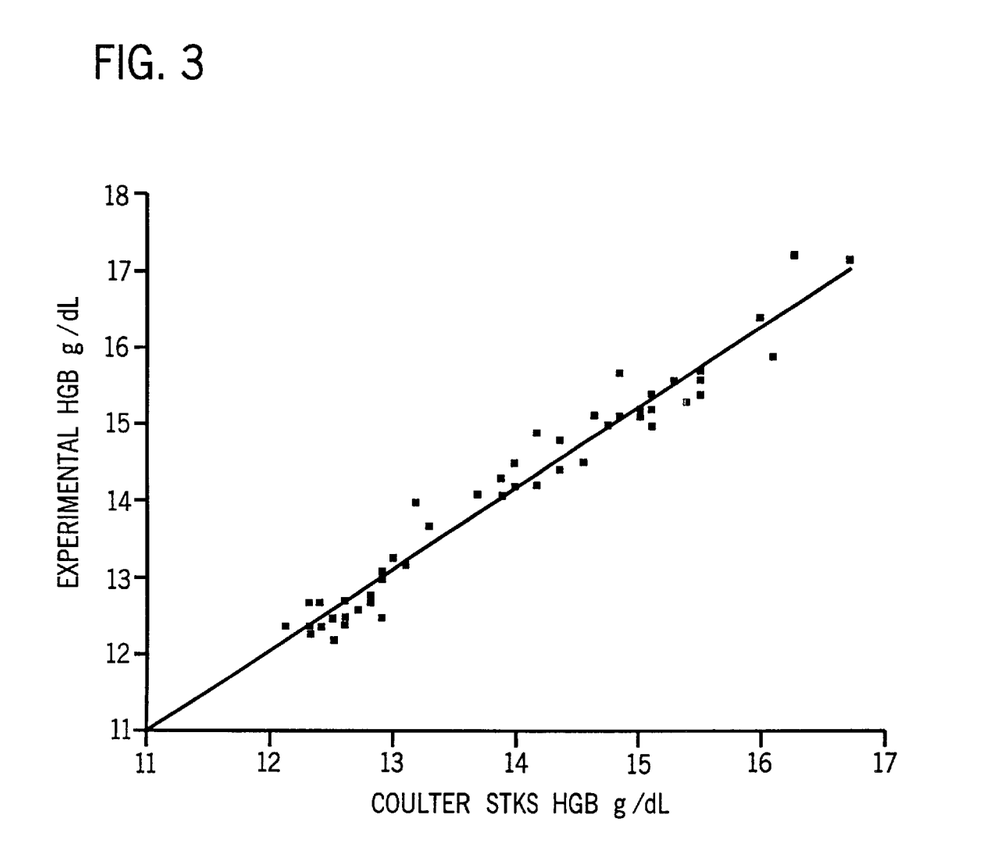
FIG. 3 is a correlation plot of hemoglobin data obtained using the cyanide-containing hemoglobin method performed on a Coulter STKS vs. the instant cyanide-free hemoglobin method performed on an experimental, automated hematology analyzer.

Fifty-two clinical samples, whose hemoglobin concentration ranged from 12 g/dL to 17.5 g/dL, were analyzed on a calibrated Coulter STKS system, a fully automated hematology analyzer in the market, and also on a calibrated experimental hematology analyzer under development with the current invention (as in EXAMPLE 8). Coulter STKS hemoglobin reagent contains potassium cyanide and the reactant of blood hemoglobin is cyanmethemoglobin. The detection wavelength of the reactant is 540 nm. The experimental hemoglobin reagent contains 0.4 moles of imidazole, 0.1 mole of sodium hydroxide, and 0.1% (w/v) lauryl dimethylamine oxide. The pH of the reagent was 13.0 without adjustment. The whole blood dilution factor for hemoglobin in the system is 1:125 and the reaction time is 10 seconds. The detection wavelength of the converted chromogen is 540 nm. The hemoglobin results of the experimental analyzer were then compared to that of the Coulter STKS by linear regression analysis. As can be seen in the regression statistics in FIG. 3, the performance of the two methods is essentially equivalent. Correlation coefficient=0.98; Slope=1.02; and Y-Intercept=−0.21.

The strong linear correlation demonstrates that the current invention gives results strictly comparable to that of the cyan met hemoglobin method of the well known commercial hematology instrument.

EXAMPLE 10

Twelve clinical samples whose hemoglobin concentration ranged from 7.0 to 17.6 g/dL were analyzed on a calibrated experimental analyzer system (as in EXAMPLE 8) using a freshly prepared hemoglobin reagent containing 0.4 moles of imidazole, 0.1 mole of sodium hydroxide and 0.1% (w/v) of lauryl dimethylamine oxide in deionized water. The pH of the reagent was 13.0 without adjustment. The same twelve samples were rerun, without re-calibration, with a hemoglobin reagent of the same composition but aged at ambient temperature for six months to evaluate the stability of the reagent.

Figure 4:
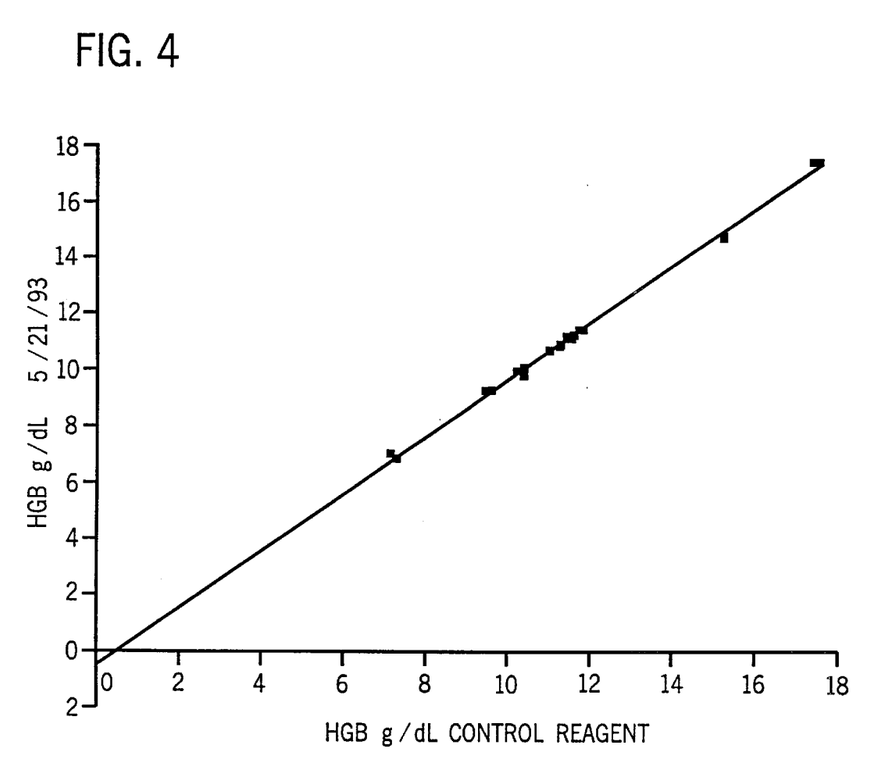
FIG. 4 is a correlation plot of the hemoglobin data for a fresh preparation control of the cyanide-free hemoglobin reagent of this invention vs. a six (6) month old preparation of the cyanide-free reagent.

The results of the control reagent was compared to that of the six months old test reagent and the linear regression data are presented in FIG. 4. No significant difference was found between the two runs, indicating that the reagent is stable at least six months at ambient temperature. Correlation coefficient=0.998; Slope=1.01; and Y-Intercept=−0.27.

EXAMPLE 11

To check the stability of the reagent of the current invention containing 0.4 moles of imidazole, 0.1 mole of sodium hydroxide and 0.1% (w/v) of lauryl dimethylamine oxide in deionized water, the conversion time and the spectrum of the converted chromogen in a less than one month old reagent was compared to that of the reagent stored for three months at 45° C. For this study, twenty four (24) microliters of a fresh normal blood was placed in a cuvette and 3.0 ml of the appropriate reagent was rapidly added from a serological pipette. Then, the reaction mixture was mixed with two aspiration/dispense cycles with a Pasteur pipette.

Figure 5A:
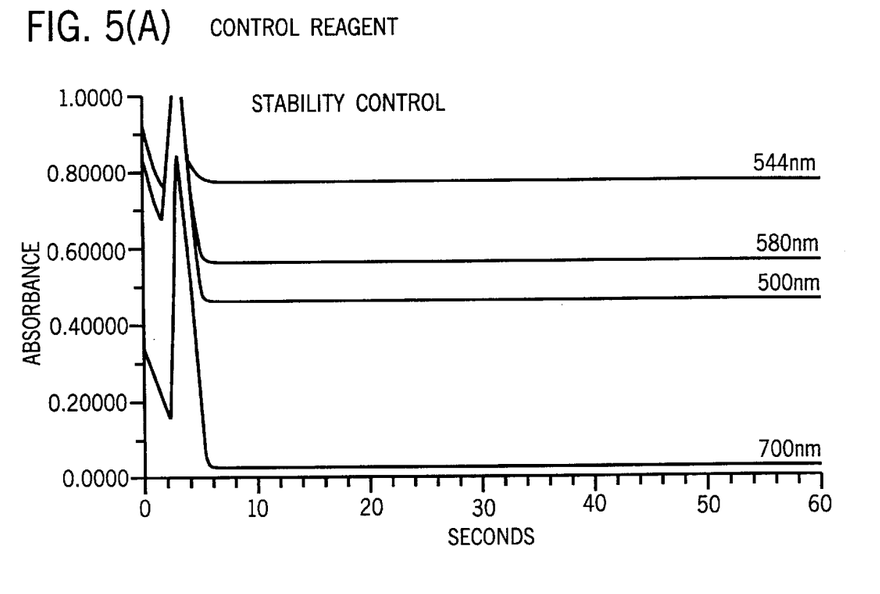
FIGS. 5A and B show the kinetics of reaction for a control and the cyanide-free hemoglobin reagent of the present, invention, when stored at 45° C. for three (3) months.
Figure 5B:
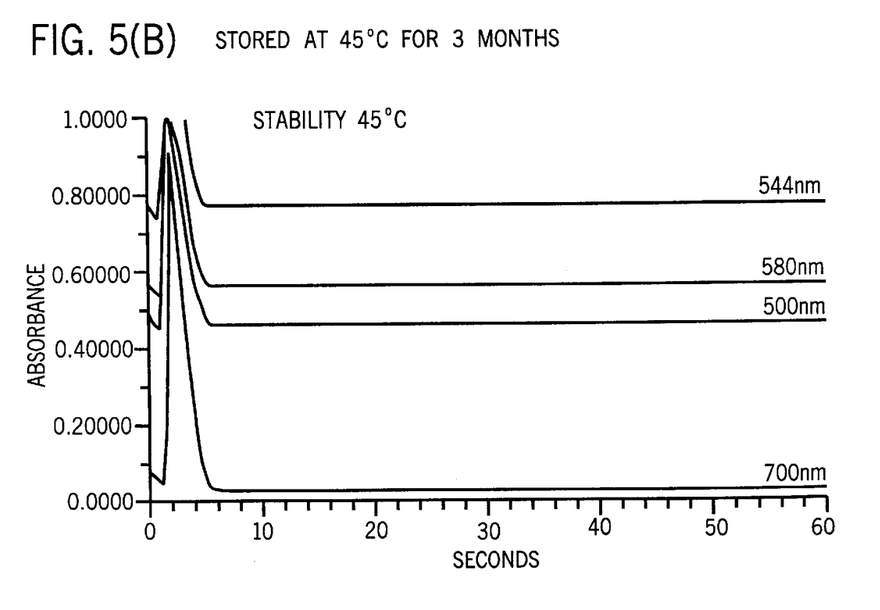

The results are presented in FIG. 5. As evidenced by the trace, mixing was complete within 10 seconds. The reaction was followed at 544 (Absorption max.), 580 (shoulder), 500 (valley), and 700 (turbidity check) nm (top to bottom traces). The 700 nm reading indicates completeness of lysis. Both control and 45° C. stored reagents appear to have identical kinetics of reaction. The conversion time was less than 10 seconds. Arrehnius' extrapolation from these data indicate that the reagent formulation of the current invention is stable for over a year at ambient temperature.

EXAMPLE 12

A normal blood sample with hemoglobin concentration of 15.8 g/dL, as determined on a calibrated Cell-Dyn 3500 system, was used to evaluate the level of turbidity interference in the hemoglobin measurement from a lipemic sample in the current invention. This is a known problem in hemoglobin measurement by many methods including ICSH cyanmethemoglobin method. Lipid-Trol (PN# L2648) was obtained from Sigma Chemical Company. The product contained 1330 mg/dl triglyceride and 840 mg/dL cholesterol. Five dilution's of the product were made with isotonic saline to the final concentrations of triglyceride and cholesterol indicated in the Table below to sufficiently cover the clinical range. Twenty (20) microliters of these solutions (20 microliters of saline was added to the control preparation) were added to the 1:125 dilution of the blood sample with the hemoglobin reagent of the current invention as in EXAMPLE 10, mixed and the optical densities of each sample was measured using a 1 cm cuvette at 540 nm (for hemoglobin) and 700 nm (for turbidity) in a Turner Model 690 spectrophotometer. The concentration of hemoglobin in each preparation was calculated using the hemoglobin value of the control (Cell-Dyn 3500 system hemoglobin value on the same blood sample).

Note that the O.D. of the converted chromogen of the current invention has a linear relationship to the concentration of hemoglobin.

| TRIG/CHOL | 540 nm O.D. | 700 nm O.D. | Hb Conc. (g/dL) |
| --- | --- | --- | --- |
| 1330/840 | 0.82 | 0.03 | 15.6 |
| 1064/672 | 0.82 | 0.03 | 15.6 |
| 798/504 | 0.82 | 0.03 | 15.6 |
| 532/336 | 0.84 | 0.03 | 15.9 |
| 266/168 | 0.82 | 0.03 | 15.6 |
| 0/0 (control) | 0.83 | 0.03 | 15.8 |

As the data show, no significant difference either in the turbidity (700 nm O.D.) measurement or in the hemoglobin value (540 nm O.D.) was observed due to the addition of triglyceride and cholesterol in these sample preparations.

EXAMPLE 13

A normal blood sample with hemoglobin concentration of 15.6 g/dL, as determined on a calibrated Cell-Dyn 3500 system, was used to evaluate the level of bilirubin interference in the hemoglobin measurement from a hyperbilirubinemia patient's sample in the current invention. This is a known problem in hemoglobin measurement by many methods including NCCLS cyanmethemoglobin method. A Bilirubin Standard (Catalog No. 550-11) was obtained from Sigma Chemical Company. The product contained 30 mg/dL bilirubin when the total content in the vial was reconstituted with 1.5 ml of de ionized water. Five dilution's of the product was made with isotonic saline to the final concentrations of bilirubin indicated in the Table below to sufficiently cover the clinical range. Twenty (20) microliters of these solutions (20 microliters of saline was added to the control preparation) were added to the 1:125 dilution's of the blood sample with the hemoglobin reagent of the current invention as in EXAMPLE 10, mixed and the optical densities of each sample was measured using a 1 cm cuvette at 540 nm (for hemoglobin) and 700 nm (for turbidity) in a Turner Model 690 spectrophotometer. The concentration of hemoglobin in each preparation was calculated using the hemoglobin value of the control (Cell-Dyn 3500 system hemoglobin value on the same blood sample). Note that the O.D. of the converted chromogen of the current invention has a linear relationship to the concentration of hemoglobin.

| Bilirubin in mg/dL | 540 nm O.D. | 700 nm O.D. | Hb Conc. in gm/dL |
| --- | --- | --- | --- |
| 0.0 (control) | 0.81 | 0.023 | 15.6 |
| 4.0 | 0.81 | 0.025 | 15.5 |
| 10.0 | 0.81 | 0.027 | 15.6 |
| 15.0 | 0.81 | 0.025 | 15.6 |
| 20.0 | 0.82 | 0.024 | 15.7 |
| 30.0 | 0.83 | 0.031 | 15.9 |

As the data show, no significant increase either in the turbidity (700 nm O.D.) measurement or in the hemoglobin value (540 nm O.D.) was observed due to the addition of bilirubin in these sample preparations. The results indicate that hyperbilirubinemia patients' samples will not interfere with the current invention in the determination of total blood hemoglobin concentration.

While certain representative embodiments and details have been shown for purpose of illustrating the invention, various changes and modifications can be made therein without departing from the scope of the invention defined in the claims.

What is claimed is:

1. A cyanide-free method of determining total hemoglobin concentration in a whole blood sample comprising the steps of:
   (a) providing a cyanide-free, added oxidizing agent-free reagent comprising an aqueous solution of:
      (i) a cyanide-free ligand selected from the group consisting of imidazole, imidazole derivatives, N-hydroxyacetamide, N-hydroxyl amine, pyridine, oxazole, thiazole, pyrazole, pyrimidine, purine, quinoline, and isoquinoline, wherein the ligand is present at a concentration of 0.1 to 2.0 Molar; and
      (ii) a surfactant selected from the group consisting of lauryl dimethylamine oxide and octylphenoxyethanol, said surfactant being present at a concentration of from about 0.1% to about 1.0% (w/v), wherein pH of the reagent is adjusted to between 11 and 14 with a monovalent base;

(b) rapidly mixing a whole blood sample with the cyanide-free, added oxidizing agent-free reagent to form a mixture containing a chromogen within ten seconds, wherein the ligand substantially completely ligates heme molecules in said blood sample;

(c) presenting the sample-reagent mixture containing the chromogen to an absorbance spectrophotometer;

(d) measuring optical density of the chromogen; and (e) determining the total hemoglobin concentration in the sample from the measured optical density of the chromogen.

2. The method of claim 1 wherein the measuring of the optical density is conducted between 540 nm and 550 nm.

3. The method of claim 1 wherein the cyanide-free ligand is imidazole.

4. The method of claim 3 wherein the imidazole is present at a concentration of 0.4M.

5. The method of claim 1 wherein the reagent surfactant is lauryl dimethylamine oxide.

6. The method of claim 5 wherein the lauryl dimethylamine oxide is present at a concentration of 0.1% (w/v).

7. The method of claim 1 wherein the cyanide-free ligand is imidazole and the reagent surfactant is lauryl dimethylamine oxide.

* * * * *